(12) United States Patent
Chomas et al.

(10) Patent No.: US 7,837,626 B2
(45) Date of Patent: Nov. 23, 2010

(54) CONTRAST AGENT MANIPULATION WITH MEDICAL ULTRASOUND IMAGING

(75) Inventors: James E. Chomas, San Francisco, CA (US); Ismayil M. Guracar, Redwood City, CA (US); Patrick J. Phillips, Sunnyvale, CA (US); John D. Marshall, Campbell, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1259 days.

(21) Appl. No.: 11/197,954

(22) Filed: Aug. 5, 2005

(65) Prior Publication Data
US 2007/0043295 A1 Feb. 22, 2007

(51) Int. Cl.
*A61B 8/00* (2006.01)

(52) U.S. Cl. ...................................... 600/458; 600/437

(58) Field of Classification Search ................... 600/458
See application file for complete search history.

(56) References Cited

U.S. PATENT DOCUMENTS

| | | | | |
|---|---|---|---|---|
| 4,483,345 A * | 11/1984 | Miwa | ......................... | 600/438 |
| 4,559,952 A * | 12/1985 | Angelsen et al. | ............. | 600/455 |
| 4,582,061 A * | 4/1986 | Fry | ............................ | 606/185 |
| 4,622,978 A * | 11/1986 | Matsuo et al. | .............. | 600/441 |
| 4,630,612 A * | 12/1986 | Uchida et al. | ............... | 600/441 |
| 5,219,401 A * | 6/1993 | Cathignol et al. | ........... | 600/439 |
| 5,276,654 A * | 1/1994 | Mallart et al. | .................. | 367/7 |
| 5,532,379 A | 7/1996 | Fujimoto | ................ | 548/304.1 |
| 5,555,534 A * | 9/1996 | Maslak et al. | ............... | 367/135 |
| 5,558,092 A | 9/1996 | Unger et al. | | |
| 5,601,086 A * | 2/1997 | Pretlow et al. | ............. | 600/458 |
| 5,675,554 A * | 10/1997 | Cole et al. | .................. | 367/138 |
| 5,947,904 A * | 9/1999 | Hossack et al. | ............. | 600/458 |
| 6,030,344 A * | 2/2000 | Guracar et al. | ............. | 600/447 |
| 6,030,345 A * | 2/2000 | Wang | ......................... | 600/454 |
| 6,171,244 B1 * | 1/2001 | Finger et al. | ................ | 600/437 |
| 6,177,923 B1 * | 1/2001 | Arenson et al. | ............. | 345/589 |
| 6,179,781 B1 * | 1/2001 | Phillips | ...................... | 600/454 |
| 6,210,334 B1 * | 4/2001 | Phillips | ...................... | 600/453 |
| 6,213,947 B1 * | 4/2001 | Phillips | ...................... | 600/443 |

(Continued)

FOREIGN PATENT DOCUMENTS

CN 1186420 7/1998

(Continued)

OTHER PUBLICATIONS von Ramm et al. "Cardiac imaging using a phased array ultrasound system. I. System design." Circulation, vol. 53, No. 2, Feb. 1976, pp. 258-262.*

(Continued)

*Primary Examiner*—Brian Casler
*Assistant Examiner*—Jonathan G Cwern

(57) ABSTRACT

Contrast agents are manipulated with acoustic radiation force while ultrasound imaging. Continuous waves for acoustic radiation force are transmitted. Substantially simultaneously, pulsed waves for imaging are transmitted. Low mechanical index continuous and pulsed waves may be used to increase binding efficiency of drug containing contrast agents with the tissue for treatment. Various techniques may be used to minimize the effect of the continuous waves on imaging with the pulsed waves. The acoustic radiation force may be transmitted with an amplitude profile and/or unfocused or defocused.

24 Claims, 2 Drawing Sheets

U.S. PATENT DOCUMENTS

| | | | |
|---|---|---|---|
| 6,371,912 B1 | 4/2002 | Nightingale et al. | |
| 6,436,041 B1* | 8/2002 | Phillips et al. | 600/437 |
| 6,491,633 B1* | 12/2002 | Krishnan et al. | 600/447 |
| 6,494,841 B1* | 12/2002 | Thomas et al. | 600/447 |
| 6,497,666 B1* | 12/2002 | Phillips et al. | 600/458 |
| 6,511,428 B1* | 1/2003 | Azuma et al. | 600/439 |
| 6,517,489 B1* | 2/2003 | Phillips et al. | 600/458 |
| 6,602,195 B1* | 8/2003 | Krishnan et al. | 600/447 |
| 6,626,836 B2* | 9/2003 | Mao et al. | 600/455 |
| 6,632,177 B1* | 10/2003 | Phillips et al. | 600/458 |
| 6,638,228 B1* | 10/2003 | Brock-Fisher et al. | 600/443 |
| 6,679,844 B2* | 1/2004 | Loftman et al. | 600/443 |
| 6,682,482 B1 | 1/2004 | Krishnan | |
| 6,716,168 B2 | 4/2004 | Nock et al. | |
| 6,726,629 B1* | 4/2004 | Frinking et al. | 600/458 |
| 6,962,071 B2* | 11/2005 | Frinking et al. | 73/24.01 |
| 2001/0021371 A1* | 9/2001 | Eriksen et al. | 424/9.52 |
| 2001/0039381 A1* | 11/2001 | Burns et al. | 600/443 |
| 2005/0020945 A1* | 1/2005 | Tosaya et al. | 601/2 |
| 2005/0055178 A1 | 3/2005 | Phillips et al. | |
| 2005/0124884 A1* | 6/2005 | Bolorforosh et al. | 600/439 |
| 2005/0245828 A1* | 11/2005 | Tsujino | 600/453 |
| 2005/0273010 A1* | 12/2005 | Shi et al. | 600/458 |
| 2006/0051879 A9 | 3/2006 | Koster et al. | 436/518 |
| 2006/0253026 A1* | 11/2006 | Gueck et al. | 600/439 |

FOREIGN PATENT DOCUMENTS

| | | |
|---|---|---|
| DE | 29 46 622 | 5/1981 |
| DE | 29 46 662 | 5/1981 |
| EP | 0 335 578 | 10/1989 |
| EP | 0335578 A2 * | 10/1989 |
| JP | 58026238 | 2/1983 |

OTHER PUBLICATIONS

Alley et al., "Mapping protein-protein interactions in the bacteriophage T4 DNA polymerase holoenzyme using a novel trifunctional photo-cross-linking and affinity reagent" J. Am. Chem. Soc. 122:6126-6127 (2000).

Horney et al., "Synthesis and characterization of Insulin-like Growth Factor (IGF)-1 photoprobes selective for the IGF-binding proteins (IGFBPs)" J. Biol. Chem. 276(4):2880-2889 (2001).

Larsson et al., "Use of an affinity proteomics approach for the identification of low-abundant bacterial adhesins as applied on the Lewis$^b$-binding adhesin of *Helicobacter pylori*" FEBS Letters 469:155-158 (2000).

Santhoshkumar et al., "Identification of a region in alcohol dehydrogenase that binds to α-crystallin during chaperone action" Biochimica et Biophysica Acta 1598:115-121 (2002).

Sugimoto et al., "Syntheses of novel photoaffinity probes for bioorganic studies on nyctinasty of leguminous plants" Tet. Lett. 43:6529-6532 (2002).

H. Von Bibra, G. Setherland, H. Becher, J. Neudert, and P. Nihoyannopoulos, Clinical Evaluation of Left Heart Doppler Contrast Enhancement by a Saccharide-Based Transpulmonary Contrast Agent, J. Am Coll Cardiol, vol. 25, 1995 pp. 500-508, XP002400913.

Vonramm O., Thurstone F., Cardiac Imaging Using A Phased Array Ultrasound System. I. System Design. Circulation, vol. 53, No. 2, Feb. 1976, pp. 258-262, XP002400914.

CA. Kleinkauf-Houcken, B. Hüneke, Ch. Linder, and W. Braendle, Combining B-Mode Ultrasound With Pulsed Wave Doppler for the Assesment of Tubal Patency, Human Reproduction, vol. 12 No. 11 pp. 2457-2460, 1997XP-002400915.

"Radiation Force Assisted Targeting facilitates Ultrasonic Molecular Imaging," by Shukui Zhao et al.; Molecular Imaging; vol. 3, No. 3; pp. 1-14; dated Jul. 5, 2004.

U.S. Appl. No. 10/899,803, filed Jul. 26, 2004.

U.S. Appl. No. 10/944,072, filed Sep. 17, 2004.

U.S. Appl. No. 11/123,585, filed May 4, 2005.

Examiner's Office Action dated Dec. 4, 2009 (including translation) for Chinese counterpart patent application No. 200680036891.X, filed Apr. 12, 2006; total pages 14.

* cited by examiner

CONTRAST AGENT MANIPULATION WITH MEDICAL ULTRASOUND IMAGING

BACKGROUND

This present embodiments relate to manipulating contrast agents. For contrast agents with drugs, fragmentation of the contrast agents away from the tissue for treatment is generally not desired. Release of drugs in a center of a vessel may lead to the drugs not being applied to the desired vessel wall.

Acoustic radiation force is used to displace the contrast agents towards the tissue to be treated or into a greater concentration, but while minimizing destruction. Acoustic radiation force may improve the binding efficiency of targeted contrast agents, such as increasing a number of drug filled contrast agents that bind with a vessel wall, activated endothelium or other area.

Radiation force increases with greater resonance with the contrast agents. The displacement increases linearly with increasing pulse length. Greater resonance and long pulse length may be used for displacement while minimizing fragmentation. Fragmentation is weakly a function of pulse length, such as the contrast agent slowly shrinking due to the acoustic radiation force until the frequency of the force is low relative to the resonant size of the contrast agent. Fragmentation is more strongly a function of the mechanical index, or the peak negative pressure divided by the square root of the center frequency. Therefore, low mechanical index is used for generating radiation force without destroying the contrast agent.

Low mechanical index B-mode imaging of contrast agents may allow imaging of contrast agents while minimizing destruction. Pulsed waves are used for imaging. Contrast agents have been imaged in combination with application of therapeutic ultrasound energy. The imaging and therapy pulses are sequentially transmitted. The therapy pulses are used to increase a temperature and associated uptake characteristic of tissue for drug delivery.

BRIEF SUMMARY

By way of introduction, the preferred embodiments described below include methods, systems and instructions for manipulating contrast agents while ultrasound imaging or for manipulating contrast agents with ultrasound. Continuous waves for acoustic radiation force are transmitted. Substantially simultaneously, pulsed waves for imaging are transmitted. Low mechanical index continuous and pulsed waves may be used to increase binding efficiency of drug containing contrast agents with the tissue for treatment. Various techniques may be used to minimize the effect of the continuous waves on imaging with the pulsed waves. The acoustic radiation force may be transmitted with an amplitude profile and/or unfocused or defocused.

In a first aspect, a method is provided for manipulating contrast agents and ultrasound imaging. Continuous wave acoustic signals are transmitted to a region including contrast agents. Substantially simultaneously with the continuous wave acoustic signals, pulsed wave acoustic signals are transmitted to the region.

In a second aspect, a method is provided for manipulating contrast agents and ultrasound imaging. Contrast agents are manipulated or displaced with acoustic radiation force while minimizing fragmentation of the contrast agents. A multiple dimensional region including the contrast agents is imaged substantially simultaneously with manipulating the contrast agents.

In a third aspect, a method is provided for manipulating contrast agents with ultrasound. Continuous wave acoustic radiation force is transmitted from a transducer to a region including contrast agents. The transmission is performed with an unfocused or a defocused wavefront from the transducer.

In a fourth aspect, a method is provided for manipulating contrast agents with ultrasound. Acoustic radiation force is transmitted from a plurality of elements to a region including contrast agents. The transmitting is performed with an amplitude profile, at a face of the plurality of elements, with a first generally wedge shape.

The present invention is defined by the following claims, and nothing in this section should be taken as a limitation on those claims. Further aspects and advantages of the invention are discussed below in conjunction with the preferred embodiments and may be later claimed.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A transducer, system and method generate acoustic radiation force. The acoustic radiation force is directed to a region to increase targeted contrast agent binding efficiency. Continuous waves are used to provide low mechanical index with a large number of cycles to increase displacement. Defocusing the continuous wave beam further reduces the mechanical index while increasing the number of cycles applied to the contrast agents. Imaging is provided at a same time to monitor the tissue, vessel or efficacy of the targeting. Pulsed waves are transmitted and received for low mechanical index imaging while the continuous waves are transmitted. Since both low mechanical index acoustic radiation force and imaging pulses use low transmit power to limit fragmentation of contrast agents, a same power supply may be utilized in both modes.

Figure 1:
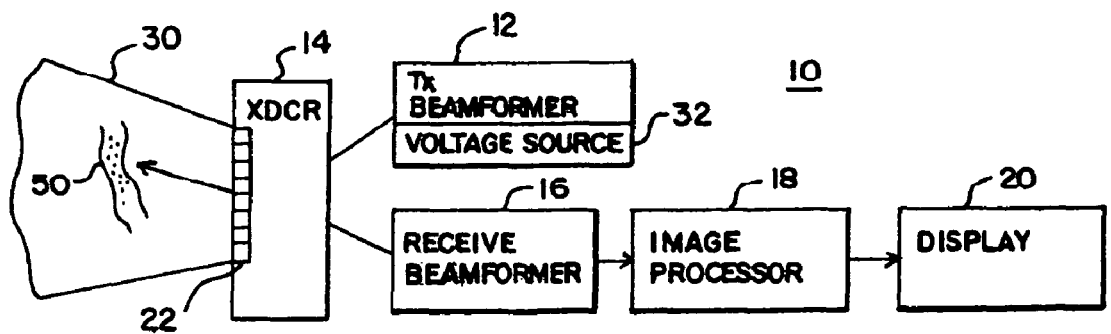
FIG. 1 is a block diagram of one embodiment of a system for manipulating contrast agents and imaging with ultrasound.

FIG. 1 shows an ultrasound system 10 for contrast agent manipulation and imaging using ultrasound energy. The system 10 includes a transmit beamformer 12, a transducer 14, a receive beamformer 16, an image processor 18, and a display 20 electrically connected as shown. Additional, different or fewer components may be provided for the system 10. In one embodiment, the system 10 comprises a medical diagnostic ultrasound system.

The transducer 14 is a piezoelectric or a capacitive micro electromechanical ultrasound transducer. The transducer 14 has one or more elements 22 for transducing between electrical and acoustical energies. In one embodiment, the transducer 14 includes a single linear array of elements 22, such as a flat or a curved linear array. In other embodiments, the transducer 14 is a two-dimensional array, a 1.5 dimensional array or other multi-dimensional configurations of elements 22. The array of elements 22 is configured for insertion into a patient or use external to a patient with or without mechanical rotation or position tracking devices.

The transducer 14 is a standard imaging transducer, such as a transducer associated with half wavelength spacing of elements 22 sandwiched between a backing block for absorbing acoustic energy and one or more matching layers for matching the acoustic impedance of the elements 22 to a patient.

Figure 6:
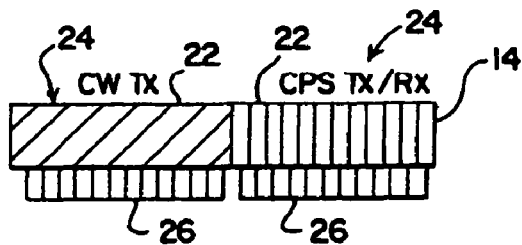
FIG. 6 shows one embodiment of a transducer for both continuous and pulsed wave use.

In an alternative embodiment, the elements 22 of the transducer 14 are separated into two or more sub apertures 24 as shown in FIG. 6. The different sub apertures 24 may be used for transmitting different types of waves, such as one sub aperture 24 for pulsed waves and another sub aperture 24 for continuous waves. The ground connections 26 are common for each sub aperture 24 but separated between the sub apertures 24. The ground connections 26 are static or switchable. Switchable ground connections 26 allow for dynamic assignment of the sub apertures 24. The separate ground connections 26 may reduce interference of the continuous wave signals with the imaging transmit and receive operation associated with the pulsed waves.

Figure 7:
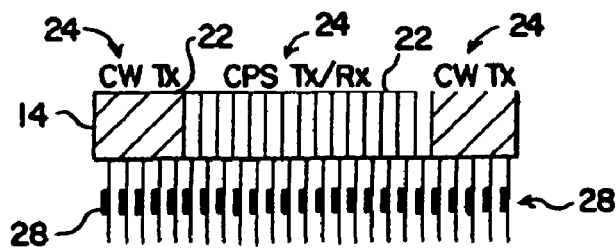
FIG. 7 shows another embodiment of a transducer for both continuous and pulsed wave use.
Figure 8:
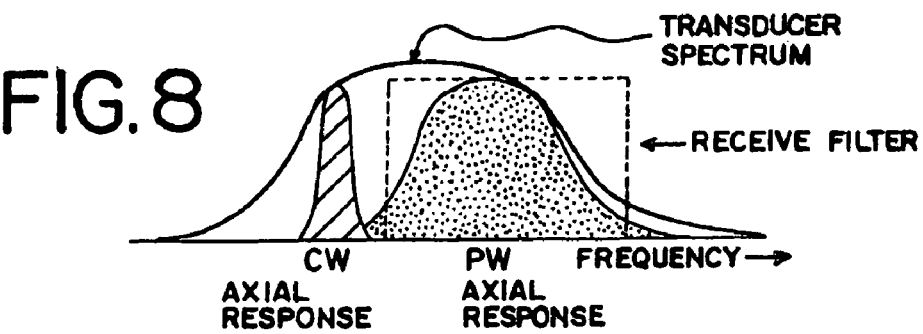
FIG. 8 is a graphical representation of frequency responses for continuous and pulsed wave transmissions.

FIG. 7 shows another alternative embodiment. The sub apertures 24 are static or dynamic. All or some of the elements 22 include filters 28 to reduce interference from the continuous waves in the elements 22 used for receiving pulsed wave echoes. The filters 28 are analog filters, such as capacitors, inductors and/or resistors for filtering out energy at the continuous wave frequencies. For example, the matching network in the transducer 14 or the transducer connector is modified by selecting appropriate inductance or capacitance components to filter out the continuous wave band of frequencies, such as 1-2 MHz. For example, FIG. 8 shows a receiver filter response relative to a continuous wave and a pulsed wave axial response. The filtering is performed for receive operations on a receive path.

In yet other embodiments, one or more elements 22 between each sub aperture 24 are disconnected or dead to avoid acoustical cross talk. Different sub apertures 24 may be provided on different sub arrays. The elements 22 or transducer structure of each sub array are optimized, such as through element size, shape, type, matching layer, lens or material, to operate at different frequency bands or with different spectral sensitivities for continuous and pulsed wave operation. Bi- or multi-layer elements 22 may be used to provide different spectral sensitivity for different sub apertures 24. For example, the continuous wave transmit signal is applied to both transducer layers of a bi-layer element 22. For pulsed wave operation, a 180 degree or other phase shift is applied between the transducer layers for both transmit and receive operation. Any one or more of the different embodiments of the transducer 14 for minimizing interference may be used, such as providing combinations of two or more of the embodiments.

The transducer 14 is designed for operation within a frequency band. For example, FIG. 8 shows a transducer spectrum. The bandwidth of the transducer covers the continuous wave and pulsed wave bands, such as extending from 1-4 MHz. Other bandwidths are possible.

The transmit beamformer 12 is a waveform generator, pulser, digital-to-analog converter, switches or other source of electrical excitations for imaging and acoustic radiation force transmissions. For imaging, the transmit beamformer 12 generates waveforms for each of a plurality of channels or transducer elements 22, such as 128 pulsed waveforms, separately delayed and apodized for focusing transmissions along scan lines within a field of view 30. Based on the delays and apodization, multiple transmissions may be sequentially scanned across substantially parallel scan lines in the entire field of view 30. The field of view 30 is formed in response to the scan pattern, such as a linear, sector or Vector® scan patterns. The different waveforms are provided to the elements 22 in the sub aperture 24 for pulsed wave operation.

For acoustic radiation force, the transmit beamformer 12, using the same or different components, also generates one or more continuous waves. For example, continuous waves are generated for each of a plurality of elements 22 in one or more sub apertures 24 for continuous wave transmission. The continuous waves are continuous in that the waves are substantially longer than pulsed waves, such as pulsed waves include 1-5 cycles and continuous waves including 20 or more cycles. A continuous wave may have a beginning and an end. The continuous waves are focused through apodization and/or relative phasing. In other embodiments, the continuous waves are defocused or unfocused, such as associated with a diverging wavefront or a substantially infinite focus.

Referring again to FIG. 1, the transmit beamformer 12 includes a power supply 32 for generating low mechanical index acoustic transmissions. For example, the power supply 32 provides 0.1-20 volts for each channel or element 22. The power supply 32 is operable for pulsed or continuous waves and is programmable, such as being programmable to provide different voltage levels as a function of an apodization profile and/or as a function of continuous or pulsed waveform operation. The same power supply 32 is provided for both types of waves, or different power supplies are used for the different types of waveforms (e.g., 0.1-5 volts for continuous waves and 0.1-15 volts for pulsed waves). Alternatively, the power supply 32 is operable for generating larger acoustic amplitudes, such as associated with 100 or 200 volt peaks.

The transmit beamformer 12 electrically connects with the transducer 14 for generating transmissions of acoustic energy or transmit pulses in response to the electrical signals from the transmit beamformer 12. The acoustic energy transmitted includes one of imaging or acoustic radiation force pulses. Imaging pulses are transmissions adapted for generating an image of the field of view 30, such as sequential transmissions of narrow beams sequentially focused along a plurality of scan lines. Acoustic radiation force pulses include transmissions adapted for displacing contrast agent and/or enhancing drug delivery.

The receive beamformer 16 generates receive beams for imaging. The receive beamformer 16 applies various delays and apodization to electrical signals received from elements 22 of the transducer 14 for the pulsed wave sub aperture 24 and sums the signals to generate a receive beam representing one or more scan lines in response to each of the pulsed wave transmissions.

The image processor 18 is one or more of an application specific integrated circuit, general processor, digital signal processor, memory, filter, other digital circuitry, analog circuitry, a combination thereof or other devices for detecting and processing information from the received, beamformed signals for imaging. In one embodiment, the image processor 18 is a B-mode or Doppler detector. For example, the amplitude of an envelope associated with the received signals is detected. As another example, a frequency shift or velocity, magnitude of a Doppler signal or energy, or variance is detected by Doppler or correlation processing for flow or tissue motion imaging. As yet another example, multiple transmit pulse with different amplitudes and/or phasing is used to identify information at selected odd, even or other harmonics using a B-mode or Doppler detector, such as disclosed in U.S. Pat. No. 6,602,195, the disclosure of which is incorporated herein by reference. Other processors for one-dimensional, two-dimensional or three-dimensional imaging may be used.

A two or three-dimensional image is generated using any of the B-mode, Doppler or other imaging methods. The detected information from the processor 18 is provided to the display 20. An image representative of the imaging pulses is generated on the display. Various combinations or single types of images are displayed substantially simultaneously, such as one or more of a B-mode or Doppler image.

Using the system 10 described above, the field of view 30 is imaged. The imaging system 10 and the same transducer 14 provide acoustic output for imaging and to manipulate contrast agents. Any of various imaging methods are used to identify a region of interest. Acoustic radiation force is used within the localized region of interest to displace contrast agents. The displacements increase the binding efficiency for selected tissue and/or increase a concentration of contrast agents in a region. By localizing contrast agents, drugs carried by or used to form the contrast agents are most effective where needed, minimizing drug dosages or side effects outside of the region of interest.

Figure 2:
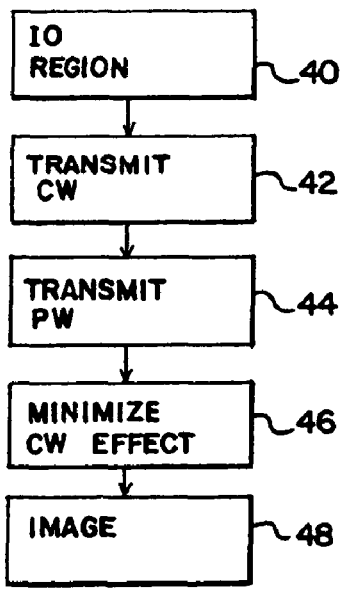
FIG. 2 is a flow chart diagram of one embodiment of a method for manipulating contrast agents and imaging with ultrasound.

FIG. 2 shows a method for manipulating contrast agents and ultrasound imaging or for manipulating contrast agents with ultrasound. The method is implemented using the system 10 shown in FIG. 1 or a different system. Additional, different or fewer acts may be provided. For example, the method is provided without acts 40, 44, 46 and/or 48. The acts are performed in the same or different order, such as performing acts 42 and 44 substantially simultaneously or simultaneously.

In act 40, the region 50 for application of acoustic radiation force is identified. The imaging field of view 30 is scanned and imaged, such as using B-mode imaging with pulsed waves. The region 50 is a vessel, chamber, organ or other part of the patient. The region 50 is identified by user selection, such as placing a border or selecting a point associated with the region 50. Alternatively, the region 50 is identified automatically by thresholding, border detection, flow detection or other image processing. The region 50 is identified with or without contrast agents being in the region 50.

Prior to, during or after the scan, contrast agents are injected, ingested or otherwise provided into the patient. The contrast agents are microspheres or other agents with or without drugs. The contrast agents have fairly uniform or diverse sizes, such as being 1-5 microns in diameter. The contrast agents are provided upstream or at the region 50 of interest. A single bolus or more continuous stream of contrast agents is provided.

In act 42, contrast agents are manipulated with acoustic radiation force. Acoustic radiation force is transmitted as continuous wave acoustic signals to the region 50 with contrast agents. The transmission may begin before contrast agents enter the region 50. The continuous waves are steered or directed towards the region 50 based on the identification of the region 50. Alternatively, the continuous waves are applied generally within a specific portion of or the entire field of view 30. The continuous wave acoustic signals operate as transmit only waves for displacing contrast agents, such as pushing the contrast agents away from the transducer 14, along a beam direction or away from a beam as a function of the wavefront.

The field of application of the acoustic radiation force from the transducer may be controlled for manipulating the contrast agents. The continuous waves are transmitted from a plurality of elements with an amplitude profile set to generate the desired energy fields, such as having spatial variation across the transducer 14. The continuous waves are unfocused, but defocused or focused beams may be used with the amplitude profile. The amplitude profile 54 at the face of the elements has a generally wedge shape in the embodiments shown in FIGS. 3 and 4. Other spatial variations in the amplitude profiles may be used, including one or two dimensional spatial variation. Alternatively, a uniform profile is provided. The amplitude profile 54 is generated as a function of a voltage profile of the transmit beamformer.

Figure 3:
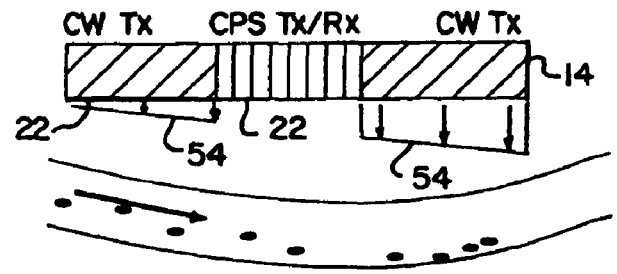
FIG. 3 is a graphical representation of one example amplitude profile for acoustic radiation force.

The wedge shape has a linear (shown), curved or nonlinear shape extending from a lesser value at or adjacent to one edge and a greater value at or adjacent to another edge. In FIG. 3, the two sub apertures 24 for continuous wave operation each have a generally wedge shape forming a generally wedge shaped profile across the entire continuous wave sub aperture 24. By providing a higher power at one edge, such as a down-stream edge relative to a vessel, the contrast agents are forced away from the transducer as well as towards the lower amplitude portion of the continuous wave beam. Contrast agents undergoing the greatest shear forces from blood flow may be subjected to the higher amplitude continuous waves, increasing attachment to the vessel wall generally at the tissue by the highest amplitude.

Figure 4:
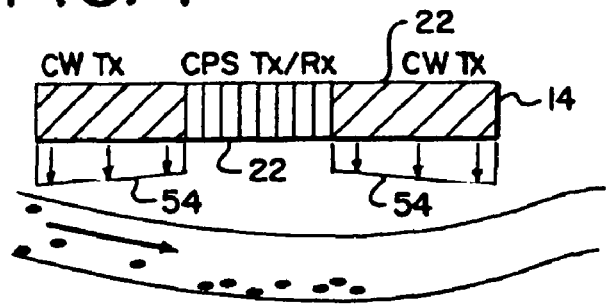
FIG. 4 is a graphical representation of another example amplitude profile for acoustic radiation force.

In FIG. 4, the two sub apertures 24 for continuous wave operation each have a generally wedge shape facing each other. The highest powers are on the outside edges of the sub apertures 24 (i.e., the edges furthest away from the other sub aperture 24), and the lowest powers are on the inside or closest edges of the sub apertures 24. The higher powers are provided on the outer edges of the continuous wave beam and the weaker powers are provided in a center of the beam. The displacement from the acoustic radiation force tends to congregate the contrast agents slightly down stream from the center of the beam in the weaker portion of the field.

In act 44, pulsed wave acoustic signals to the region 50 and/or the field of view 30. Any of various imaging pulses are transmitted. For example, pulses for B-mode or Doppler imaging are transmitted. For B-mode imaging, a 1-5 cycle pulse is transmitted along each of the scan lines within the field of view 30. For Doppler imaging, a plurality of transmit pulses for determining a Doppler coefficient, correlation or flow characteristic are transmitted along each scan line. Other imaging pulses are possible. The transmit pulses have a transmit power determined from the number of cycles, amplitude and pulse repetition frequency of the transmit pulses. The transmit pulse pressure is limited by the Food and Drug Administration to particular mechanical indexes within the field of view. Typically, ultrasound systems provide a transmit pressure near the maximum mechanical index. To avoid fragmentation, the pulsed wave acoustic signals have a transmit pressure less than the mechanical index where fragmentation occurs. For example, a particular contrast agent may have a contrast agent fragmentation threshold of 0.4; therefore, an example pulsed wave should have an MI less than 0.4 to avoid fragmentation.

A multi-dimensional image is generated in response to echoes from the pulsed wave acoustic signals. The field of view 30 is determined by the position of the transducer 14, the steering of the imaging transmissions and the selected depths of viewing. The field of view 30 is optimized to view a potential region of interest and surrounding tissue. The received echoes from the field of view 30 are detected, scan converted or otherwise processed to generate a two dimensional image or a three dimensional representation.

The imaging or pulsed wave transmissions of act 44 and associated receive events are performed substantially simultaneously with the transmission of continuous wave acoustic signals in act 42. Substantially simultaneous includes simultaneous or overlapping transmissions for at least one continuous wave element and one pulsed wave element. Due to steering, generation of acoustic energy by some elements within the pulsed or continuous wave aperture may not overlap in time with the generation of acoustic energy by other elements. By transmitting pulsed waves while continuous waves are transmitted, imaging during application of acoustic radiation force is provided. The user may observe the effects of the acoustic radiation force, monitor a treated area or observe contrast agents.

In act 48, a multiple dimensional region including the contrast agents is imaged substantially simultaneously with manipulating the contrast agents. Since the pulsed waves are transmitted at a substantially same time as the continuous waves, the echoes may be received substantially simultaneously with the transmission of the continuous waves. The echoes may be received after ceasing the continuous wave transmissions.

The received echoes are used for B-mode imaging, Doppler, phase inversion, pulse inversion or other imaging. For example, the imaging disclosed in U.S. Pat. No. 6,602,195, the disclosure of which is incorporated herein by reference is used. Imaging as a function of a cubic fundamental by relative amplitude weighting and/or phasing of the transmitted pulsed waves and/or received echoes. Different harmonics, including or excluding the transmitted fundamental frequencies, may be selectively included or minimized from the signals used for imaging by different combinations of number of pulses, apertures, weighting and/or phasing. For example, information is provided at non-linear fundamental or harmonic frequencies.

Figure 5:
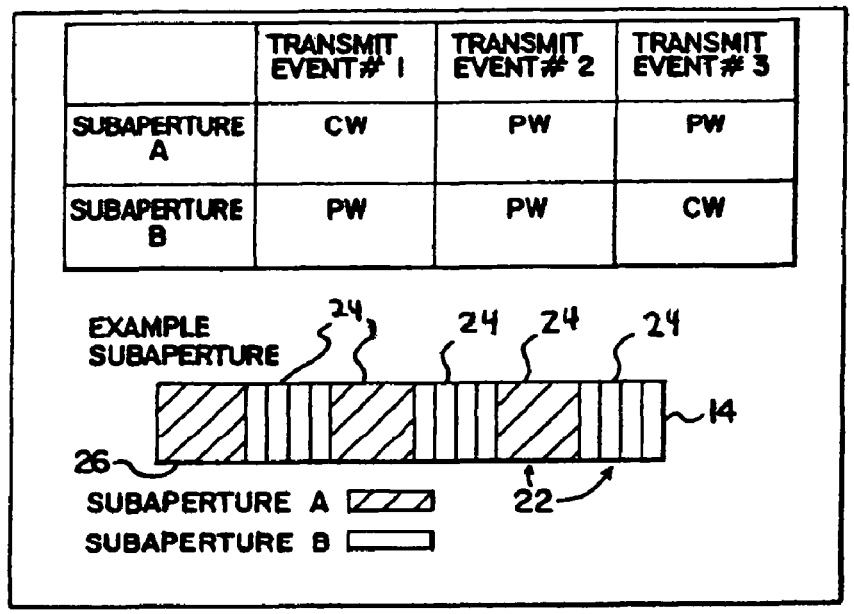
FIG. 5 is a graphical representation of an embodiment for continuous wave manipulation of contrast agents with multiple pulse pulsed wave imaging.

FIG. 5 shows one example three pulsed wave transmissions to obtain information at a desired cubic fundamental. The pulsed and continuous waves are transmitted from different sub apertures 24 on the transducer 14. The sub apertures 24 are formed as adjacent groupings of 1, 2, 4, 8 or any other number of elements The sub apertures 24 of FIG. 6 or 7 or other sub aperture divisions may be used, including sub apertures 24 having different sizes or numbers of elements.

For pulsed wave transmissions, three different transmit events along a same or adjacent scan lines are performed. One or more of the different transmissions are associated with a different transmit power level. In a first transmit event, the continuous wave transmissions are performed substantially simultaneously with the pulsed wave transmissions, but on different sub apertures 24. For a second transmit event for pulsed wave transmissions, the pulsed waves are transmitted on all of the sub apertures 24 and the continuous wave transmissions are ceased. By doubling or increasing the number of elements for pulsed wave transmissions, the power associated with the transmit event is doubled or increased. Alternatively or additionally, pulses with greater amplitude are transmitted from a fewer than all of the sub apertures. For the third transmit event, the pattern of the first transmit event is repeated, but different sub apertures 24 may be used for the substantially simultaneous transmission of both continuous and pulsed waves.

In other embodiments, other sequences of two or more pulsed wave transmit events may be used. Different relative weighting may be used. Phase variations within the sequence may be provided.

The echoes responsive to the pulsed wave transmissions are received on different sub apertures 24 than the transmissions, allowing the continuous wave transmissions to continue. The received signals are combined after beamforming. The combination is a summation, subtraction or other function. Relative phase shifts may or may not be applied to the received signals for one or a subset of the received signals. The received signals are coherently combined (i.e., combined prior to detection). By combining the signals associated with different aperture sizes and/or amplitudes, the resulting combination signals contain information with a desired response, such as cubic fundamental information more likely from contrast agents than tissue or fluid. Using low mechanical index transmissions, the contrast agents are imaged.

In act 46, the imaging is performed while minimizing echo information in the multi-dimensional images responsive to the continuous wave signals. An influence of the acoustic radiation force on the imaging is reduced by using different frequencies, different transmit directions, different delays, aperture control, wider focal region for the acoustic radiation force, a lack of focus for the acoustic radiation force, or combinations thereof. Other techniques may be used.

By transmitting the continuous wave acoustic signals from an array as defocused or unfocused signals, the energy associated with the continuous waves may be more distributed throughout the field of view 30. Unfocused or defocused signals have a divergent or planar wavefront. Relative phasing and/or apodization of the continuous waves provide the desired focus or lack of focus. The distribution may prevent or limit contrast agent destruction (i.e., reduce mechanical index for a given location) and allow use of the same power source. Since the energy is more distributed, less energy is provided along the focused or weakly focused scan locations for the pulsed waves. Alternatively, divergent or plane wave transmissions are also used for pulsed wave imaging.

Transmit delay or phasing and aperture control may be used to reduce acoustic noise from the continuous wave reflections by speckle or other reflectors in the pulsed wave scanning. The pulsed wave acoustic signals are sequentially transmitted along different scan lines, such as associated with a linear, sector or Vector® scan format. The continuous wave acoustic signals are transmitted with a wavefront sequentially angled away from a current scan line of the different scan lines for which the pulsed wave acoustic signals are transmitted. The continuous waves are steered away from the pulsed wave focus. For example, the time delay toward the middle of the transducer is increased in the start of B-mode or other pulsed wave insonification, steering the continuous wavefront away from the azimuthal midline where the pulsed waves are focused. As the pulsed wave focus changes, the steering of the continuous waves changes. As an alternative to steering the continuous wavefront, the amplitude profile of the continuous waves is altered to provide minimal power near the pulsed wave scan line.

Frequency of operation may minimize the continuous wave acoustics from the imaging. For example, the pulsed and continuous waves are transmitted at different frequencies or in different frequency bands. The frequency bands are separate, such as having −10, −20, −40 or other level of decibel point of crossover. For example, the −20 dB point on the high frequency edge of the continuous wave spectrum may cross the −20 dB point on the low frequency edge of the pulsed wave spectrum. The continuous wave transmit frequency band is lower or higher than the pulsed wave frequency band. The continuous waves more likely have a narrow bandwidth, allowing closer center frequencies. FIG. 8 shows one example where the continuous waves are centered at about 2 MHz and the pulsed waves are centered at about 4 MHz. Other frequencies may be used, such as providing the pulsed wave at a higher harmonic of the continuous wave or the continuous waves at the higher frequency to limit harmonic noise. By filtering or combining signals are receive to isolate information at the pulsed wave transmission frequencies or desired harmonics thereof, information from the continuous waves is reduced or eliminated.

By using different apertures, the effect of the continuous waves may be reduced. For example, the different ground connections reduce electrical crosstalk. A different common ground is provided for the different sub apertures or elements used for the different types of waveforms. As another example, echo signals received on the sub apertures used for the pulsed wave acoustic signals are filtered with a response operable to reduce at the frequency band of the continuous wave and pass the frequency band of the pulsed waves. As yet another example, different types elements are used for the different types of waves. The different types of elements have different spectral sensitivities, providing different apertures with different spectral sensitivities. As another example, one or more elements are not used, isolated or dead between the sub apertures to limit acoustic crosstalk. Other techniques or structures to minimize energy from the continuous waves in the pulsed wave imaging may be used.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for manipulating contrast agents and ultrasound imaging, the method comprising:

transmitting continuous wave acoustic signals to a region including contrast agents comprising ingested or injected microspheres;

displacing the contrast agents to a local area with the continuous wave acoustic signals while avoiding fragmentation of the contrast agents;

transmitting, simultaneously with the continuous wave acoustic signals, pulsed wave acoustic signals to the region; and generating an image as a function of at least the pulsed wave acoustic signals.

2. The method of claim 1 wherein transmitting the continuous wave acoustic signals and transmitting the pulsed wave acoustic signals are performed with different apertures of a same transducer.

3. The method of claim 2 wherein transmitting the continuous and pulsed wave acoustic signals comprises transmitting with the different apertures having different ground connections common within each of the different apertures.

4. The method of claim 2 wherein transmitting the continuous wave acoustic signals comprises transmitting at a first frequency band and wherein transmitting the pulsed wave acoustic signals comprises transmitting at a second frequency band, the first frequency band being separate from the second frequency band;

further comprising filtering echo signals received on the one of the different apertures used for the pulsed wave acoustic signals with a response operable to reduce at the first frequency band and pass the second frequency band.

5. The method of claim 2 wherein transmitting the continuous and pulsed wave acoustic signals comprises transmitting with elements of the different apertures having different spectral sensitivities.

6. The method of claim 1 wherein generating comprises generating a multi-dimensional image in response to echoes from the pulsed wave acoustic signals; and further comprising:

minimizing echo information in the multi-dimensional image responsive to the continuous wave signals.

7. The method of claim 1 wherein transmitting the pulsed wave acoustic signals comprises transmitting a plurality of pulses having at least two different amplitude levels;

further comprising:

combining signals responsive to the transmission of the plurality of pulses.

8. The method of claim 7 wherein transmitting the pulsed wave acoustic signals comprises transmitting from a first sub aperture and transmitting the continuous wave acoustic signals comprises transmitting from a second sub aperture different than the first sub aperture;

further comprising:

transmitting the pulsed acoustic waves from the first and second sub apertures substantially simultaneously while ceasing transmission of the continuous wave acoustic signals;

wherein combining comprises combining the signals responsive to the transmission of the pulsed acoustic waves from the first sub aperture and transmission of the pulsed acoustic waves from the first and second sub apertures.

9. The method of claim 1 wherein transmitting the continuous wave acoustic signals comprises transmitting at a first frequency band and wherein transmitting the pulsed wave acoustic signals comprises transmitting at a second frequency band, the first frequency band being separate from the second frequency band.

10. The method of claim 1 wherein transmitting the continuous wave acoustic signals comprises transmitting the continuous wave acoustic signals from an array as defocused or unfocused signals.

11. The method of claim 1 further comprising:
receiving an indication of the region from a user input;
wherein transmitting the continuous wave acoustic signals comprises transmitting as a function of the region.

12. The method of claim 1 wherein transmitting the continuous wave acoustic signals comprises transmitting from a plurality of elements with an apodization amplitude profile with a wedge shape at a face of the elements.

13. The method of claim 1 further comprising:
repeating the transmission of the pulsed wave acoustic signals sequentially along different scan lines;
wherein transmitting the continuous wave acoustic signals comprises transmitting with a wave-front sequentially angled away from a current scan line of the different scan lines for which the pulsed wave acoustic signals are transmitted.

14. A method for manipulating contrast agents and ultrasound imaging, the method comprising:
displacing contrast agents with low mechanical index acoustic radiation force while avoiding fragmentation of the contrast agents; and
imaging a multiple dimensional region including the contrast agents simultaneously with displacing the contrast agents, echoes responsive to the low mechanical index acoustic radiation force not being used for imaging.

15. The method of claim 14 wherein imaging comprises B-mode imaging.

16. The method of claim 14 wherein imaging comprises imaging as a function of a cubic fundamental.

17. The method of claim 14 further comprising:
reducing an influence of the acoustic radiation force on the imaging as a function of different frequencies, different transmit directions, wider focal region for the acoustic radiation force, a lack of focus for the acoustic radiation force, or combinations thereof.

18. A method for manipulating contrast agents with ultrasound, the method comprising:
transmitting, from a transducer, continuous wave acoustic radiation force to a region including contrast agents, the transmitting moving the contrast agents while avoiding fragmentation of the contrast agents;
performing the transmission with an unfocused or a defocused wavefront from the transducer;
transmitting, simultaneously with the continuous wave acoustic radiation force, pulsed wave acoustic signals to the region for generating an image; and
using a same power supply for transmitting the continuous wave acoustic radiation force and the pulsed wave acoustic signals.

19. The method of claim 18 further comprising imaging the contrast agents.

20. A method for displacing contrast agents with ultrasound, the method comprising:
transmitting, from a plurality of elements, acoustic radiation force to a region including contrast agents, the transmitting moving the contrast agents while avoiding fragmentation of the contrast agents;
performing the transmitting with an apodization amplitude profile with a generally wedge shape at a face of the plurality of elements, the wedge shape comprising two increases in amplitude across different sub-apertures separated by a pulsed imaging sub-aperture; and
transmitting, simultaneously with the acoustic radiation force, pulsed wave acoustic signals to the region for generating an image.

21. The method of claim 20 wherein performing comprises generating the amplitude profile as a function of a voltage profile.

22. The method of claim 20 wherein transmitting comprises transmitting from at least first and second different sub apertures of the plurality of elements, and performing comprises providing the first generally wedge shape amplitude profile for the first sub aperture and providing a second generally wedge shape amplitude profile for the second sub aperture, the first and second generally wedge shape amplitude profiles having greater amplitudes at farther edges and lesser amplitudes at closer edges.

23. The method of claim 22 wherein transmitting comprises transmitting from at least first and second different sub apertures of the plurality of elements, and performing comprises providing the first generally wedge shape amplitude profile for the first sub aperture and providing a second generally wedge shape amplitude profile for the second sub aperture, the first and second generally wedge shape amplitude profiles forming a third wedge shape amplitude profile.

24. The method of claim 20 further comprising imaging the contrast agents.

* * * * *